US010694951B2

(12) United States Patent
Kinser et al.

(10) Patent No.: US 10,694,951 B2
(45) Date of Patent: *Jun. 30, 2020

(54) PROBE STRUCTURE FOR PHYSIOLOGICAL MEASUREMENTS USING SURFACE ENHANCED RAMAN SPECTROSCOPY

(71) Applicant: INTERNATIONAL BUSINESS MACHINES CORPORATION, Armonk, NY (US)

(72) Inventors: Emily R. Kinser, Poughkeepsie, NY (US); John U. Knickerbocker, Yorktown Heights, NY (US); Roy R. Yu, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 677 days.

This patent is subject to a terminal disclaimer.

(21) Appl. No.: 15/293,267

(22) Filed: Oct. 13, 2016

(65) Prior Publication Data

US 2018/0103848 A1 Apr. 19, 2018

(51) Int. Cl.
*A61B 5/00* (2006.01)
*A61N 5/06* (2006.01)
(Continued)

(52) U.S. Cl.
CPC .......... *A61B 5/0075* (2013.01); *A61B 5/0084* (2013.01); *A61N 1/36071* (2013.01);
(Continued)

(58) Field of Classification Search
CPC ............... A61B 5/0075; A61B 5/0084; A61B 2560/0443; A61B 5/6852; A61B 5/4848;
(Continued)

(56) References Cited

U.S. PATENT DOCUMENTS

| 6,975,898 B2 | 12/2005 | Seibel |
| 7,658,991 B2 * | 2/2010 | Zhao ..................... B82Y 30/00 428/323 |

(Continued)

OTHER PUBLICATIONS

Padnababhan, Jagannath et al., Engineering Cellular Response Using Nanopatterned Bulk Metallic Glass, ACS Nano, 2014, pp. 4366-4375, vol. 8, No. 5.

(Continued)

*Primary Examiner* — Joel Lamprecht
(74) *Attorney, Agent, or Firm* — L. Jeffrey Kelly; Otterstedt, Wallace & Kammer, LLP

(57) ABSTRACT

Surface enhanced Raman spectroscopy is employed to obtain chemical data with respect to body tissue and cells. The chemical environments of stimulation implants and drug-delivery catheters are spectroscopically monitored in real time using an implantable probe. The probe includes a surface enhancer that facilitates surface enhanced Raman spectroscopy in opposing relation to an array of optical fibers. Light emitted by the optical fibers can be employed for chemical detection and/or tissue stimulation. Wavelength and optical power are selected based on whether the probe is employed for such detection or stimulation. Fabrication of a probe assembly that enables surface enhanced Raman spectroscopy is further disclosed.

14 Claims, 6 Drawing Sheets

(51) Int. Cl.
*A61N 1/36* (2006.01)
*A61N 5/067* (2006.01)

(52) U.S. Cl.
CPC ......... *A61N 5/0601* (2013.01); *A61N 5/0622* (2013.01); *A61B 5/4848* (2013.01); *A61B 5/6852* (2013.01); *A61N 2005/063* (2013.01); *A61N 2005/067* (2013.01)

(58) Field of Classification Search
CPC .............. A61N 5/0622; A61N 1/36071; A61N 5/0601; A61N 2005/067; A61N 2005/063; A61M 5/00
See application file for complete search history.

(56) References Cited

U.S. PATENT DOCUMENTS

| | | | |
|---|---|---|---|
| 8,140,152 B2 | 3/2012 | John et al. | |
| 8,346,346 B1* | 1/2013 | Schnitzer | A61B 1/043 600/476 |
| 8,551,150 B1 | 10/2013 | Webb et al. | |
| 8,911,426 B2 | 12/2014 | Coppeta et al. | |
| 8,956,363 B2 | 2/2015 | Schneider et al. | |
| 9,451,908 B2* | 9/2016 | Kamath | A61B 5/7235 |
| 2003/0111142 A1 | 6/2003 | Horton, Jr. et al. | |
| 2006/0046311 A1* | 3/2006 | Sun | G01N 33/54366 436/518 |
| 2006/0177379 A1 | 8/2006 | Asgari | |
| 2006/0192115 A1* | 8/2006 | Thomas | G01N 21/6458 250/306 |
| 2008/0214913 A1 | 9/2008 | Martinus et al. | |
| 2013/0150230 A1 | 6/2013 | Taylor et al. | |
| 2014/0353172 A1 | 12/2014 | Melosh et al. | |

OTHER PUBLICATIONS

B & W Tek, Inc., Components of a Raman Spectrometer, 2015, downloaded Dec. 2, 2015 from http://bwtek.comlraman-components-of-a-raman-spectrometer/, pp. 1-2.

Yin, X. et al., Terahertz Imaging for Biomedical Applications: Pattern Recognition and Tomographic Reconstruction, Chapter 2, pp. 9-26, 2012, Springer Science + Business Media.

Kuo, Jinn-Rung et al., Deep brain light stimulation effects on glutamate and dopamine concentration, Biomedical Optics Express Jan. 2015 v6 n1 pp. 23-31.

Pollo, Claudio et al., Directional deep brain stimulation: an intraoperative double-blind pilot study, Brain 2014, pp. 1-12, May 19, 2014.

Reed, William A. et al., Gradient-index fiber-optic microprobes for minimally invasive in vivo low-coherence interferometry, Optics Letters, vol. 27, No. 20, pp. 1794-1796, Oct. 15, 2002.

Chiral Photonics, PROFA Pitch Reducing Optical Fiber Array-Two Dimensional (2D), www.ChiralPhotonics.com, pp. 1-5, Dec. 2015.

GRIN Tech, GRIN Rod Lenses-Numerical Aperture 0.5, Dec. 2015 pp. 1-2.

Emily R. Kinser et al. unpublished U.S. Appl. No. 15/293,261, filed Oct. 13, 2016, Probe Structure for Physiological Measurements Using Surface Enhanced Raman Spectroscopy, 29 pages plus 6 sheets drawings.

List of IBM Patents or Patent Applications Treated as Related, 2 pages, Oct. 30, 2016.

* cited by examiner

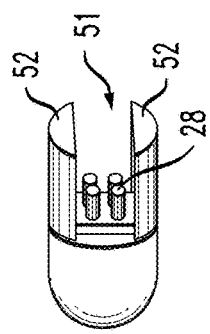
FIG. 3A
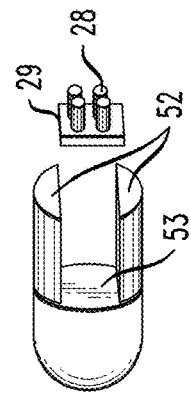
FIG. 3B
FIG. 3C
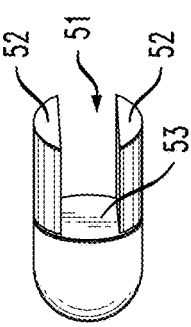
FIG. 3D
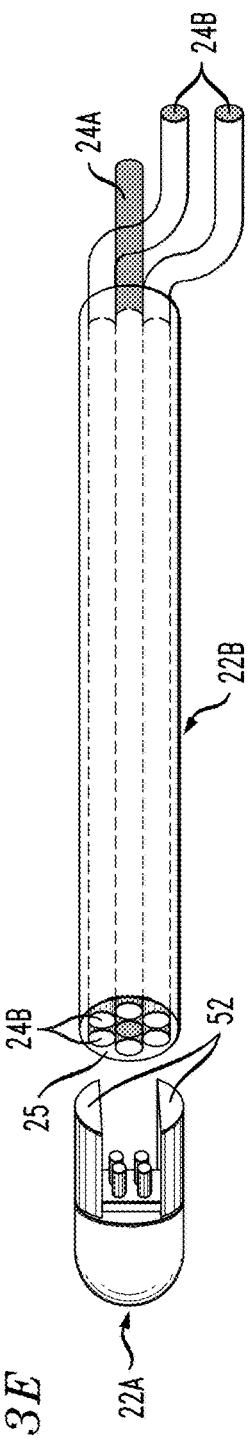
FIG. 3E
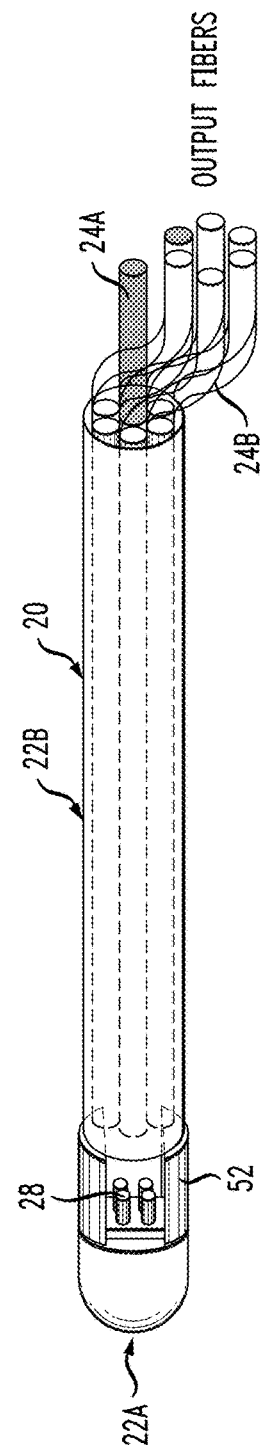
FIG. 3F

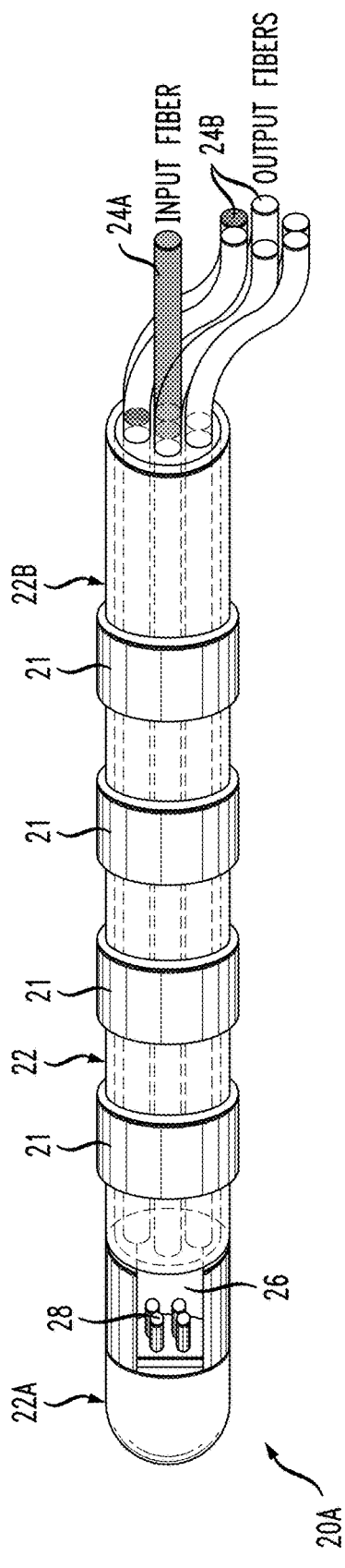
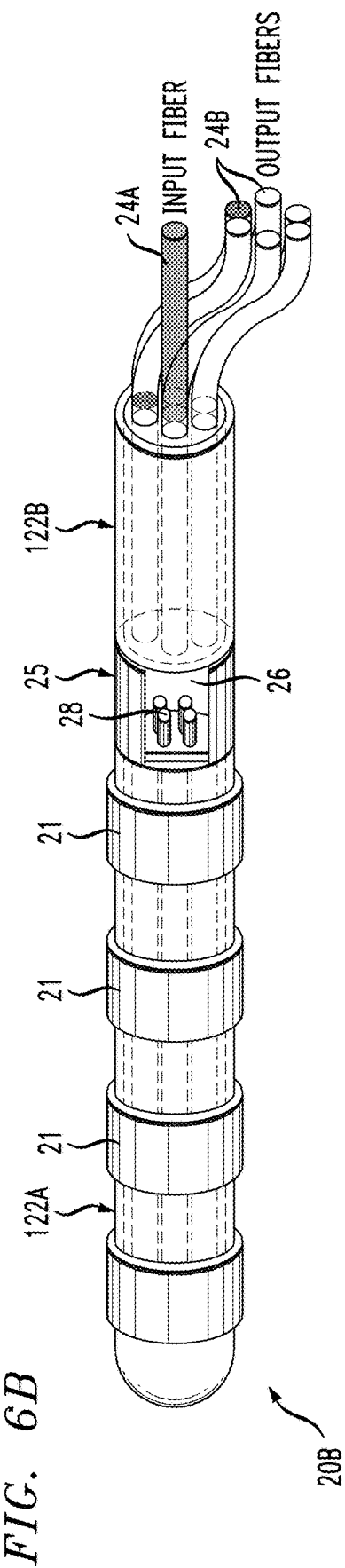
FIG. 6A
FIG. 6B

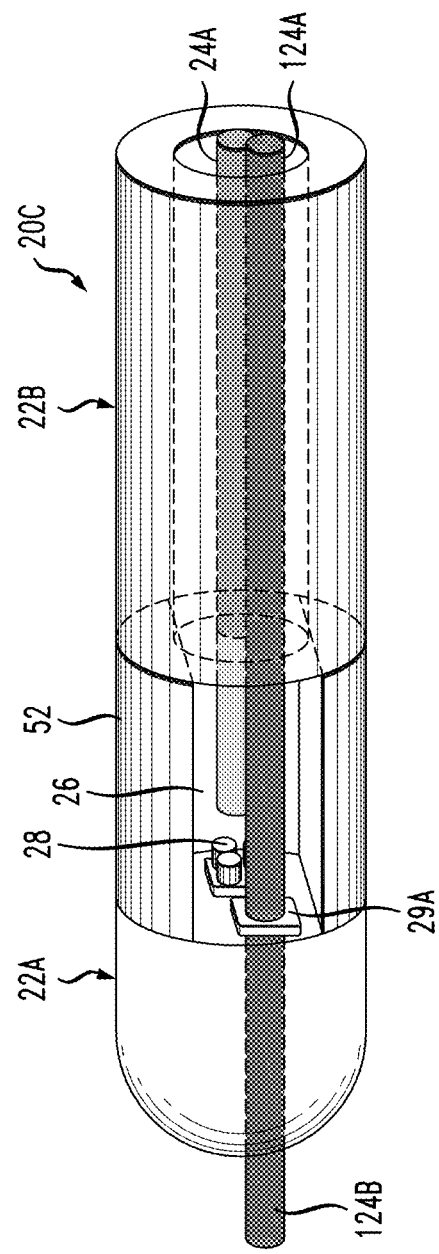

PROBE STRUCTURE FOR PHYSIOLOGICAL MEASUREMENTS USING SURFACE ENHANCED RAMAN SPECTROSCOPY

BACKGROUND

The present disclosure relates generally to implantable bio-probes for detecting the presence of biological or other chemical materials using surface enhanced Raman and surface enhanced Terahertz-Raman spectroscopies. Implantable probes are used in either steady states or in conjunction with dynamic transient processes.

Electromagnetic radiation spectrum covers a wide wavelength range, from gamma-ray, x-ray, UV, visible light, infra-red (near and far IR), terahertz (THz), to microwave and radio wave. The energy levels in the IR (10 THz to 400 THz) and THz (0.1-10 THz) regions coincide with molecular bond vibrational and rotational energies. Therefore, in science and technology the IR and Terahertz regions of the radiation spectrum are typically used for chemical and molecular structure identification. Each chemical and biological molecule and macromolecule (protein, enzyme) has its molecular vibrational and rotational energy signatures, unique finger prints to the species, detectable and identifiable in the IR and THz spectrum region.

IR spectroscopy is widely used for chemical analysis. IR spectroscopy typically uses a "white" light (a broad band with all wave lengths included) to illuminate the sample and detect the missing (absorbed) components in the spectrum, such implicating the presence of specific vibrational chemical bonds and, therefore the presence of the chemical species. These vibrational bonds can also be probed using a single wavelength laser to detect the spectrum of the scattered laser energy (called Raman scattering, or Raman spectroscopy). With the advancement of solid state lasers, such as quantum cascade lasers, and optical filters, Raman spectroscopy has become the favored technique in micro and nano scale chemical and structural analysis, due to the accuracy and stability of modern microelectronics and optics.

Raman spectroscopy typically involves the illumination of a sample with a laser beam (with a well-defined wave length and tight half-width) and collecting the radiation scattered by the illuminated sample for analysis. LabRAM® ARAMIS from Horiba Scientific is one of such instrument with microscope and stepping function. Once illuminated by the laser the electrons in the molecules in the sample can become excited and either absorb or lose a photon. When the excited molecule returns to its ground state it will emit a photon (light) with the energy unique to the structure of the emitting molecule. If a molecule absorbs a photon and reemits, it's called Stoke's emission, otherwise, anti-Stoke's emission. With the aid of a well-focused laser Raman spectra can be obtained from small volumes and allow the identification of species present in the volumes.

Terahertz spectra lay between IR and microwave in the electromagnetic spectrum. In technology, the Terahertz (sometime called mm wave) region is also termed "Terahertz gap". This is because there is almost no natural occurring radiation source for terahertz. IR radiation is produced by photon excitation which is best for >10 THz while microwave radiation by electron excitation good for <0.1 THz. Due to the difference in source and detection, THz spectroscopy is typically a different method from Raman spectroscopy which uses near-UV (NUV), visible and IR. Recently, however, a detection method has been developed by Ondax, Inc. which, using a volumetric filter, can combine Raman and THz in a single system. Low energy phonons can also be detected using a BragGrate™ Notch Filter from OptiGrate Corp., for example, in volumetric holographic grating.

Biological molecules and macromolecules (protein/enzyme) are typically very large molecules, containing thousands and millions of H, C, O, N, and other atoms with a well-defined and folded structure. Such large molecules not only exhibit molecular bond vibration, they also have collective motions (rotation, shear, breath, torsion). For a C—H bond, the vibrational energy is typically between 2700-3300 (1/cm) (or 80-100 THz) depending on the type of the molecule the bond resides. For C—C bond, the bond energy range (1200-1700 1/cm), (or 40-50 THz) also depending on the bond's environment. Typically, the heavier an atom the lower the vibrational energy, with all other factors being equal. IR Raman spectroscopy covers a range of 333-5000 1/cm. (10-150 THz). Energy below 333 1/cm (0.1 to 10 THz) belong to Terahertz domain. For very large molecules such as macromolecules, additional vibrational collective modes occur. These collective motions have energy levels low in the terahertz region (<333 1/cm, or <10 THz). Increasingly, THz spectroscopy, in conjunction with Raman spectroscopy, are used for protein and macromolecule structural analysis.

Raman spectroscopy (333-5000 1/cm) can be employed to detect the presence of biological and medical specimens, including organic molecules such as proteins, glucose, and insulin most efficiently in powder and in crystalline form. Raman is also used as light scattered in solution by analyte molecules is unique to the particular molecules, which allows the determination of the molecules that are present within solvent, tissue, or blood samples. For in-situ, in-vitro, and in-vivo analysis, surface enhanced Raman spectroscopy (SERS) can be used. Surface-enhanced Raman spectroscopy (SERS) is a technique that enhances Raman scattering by molecules interacting with rough metal surfaces or nanostructures. The enhancement mechanism relates to laser stimulated surface plasmon resonance in certain metals, Au, Ag, Pt, being most common. When the incident laser frequency coincides with the surface plasmon, strong absorption and reemission of the laser energy occurs, and so too the signals from the molecules present on such surfaces. Surface plasmon resonance has been widely used in bio-sensors for biomolecule antigens detection without the use of labeling agents. Advancements in nanotechnology have allowed nanoparticles suspended in solution and mixed with the chemical to be analyzed. The presence of the nanoparticles in the vicinity of such chemicals greatly enhances Raman detectability. It is, however, difficult to introduce suspended particles in vivo. Biomolecules such as proteins have been detected suing SERS substrates. Nanopatterned bulk metallic glass (BMG) such as Pt-BMG can enhance glucose detection. The enhancement of signals obtained using SERS technology may include different modes from those obtained using traditional non-enhancing techniques as the symmetries of detected molecules can be changed, depending on the polarity of the laser.

Implantable devices have been employed for various treatments such as deep brain stimulation (DBS), as spinal cord implants for pain management, and for muscle stimulation therapies. Patients with Parkinson's syndrome, for example, may benefit from DBS therapy. DBS therapy devices operate by providing electrical stimulation to the thalamus area of the brain via an implanted electrode to stimulate the brain's motion control function that has been reduced by cellular degeneration. Implantable devices are also used in the spinal cord for chronic pain control and in muscles to restore patient mobility lost to spinal cord injury. Coupled with micro-fluidic channels, deep implants are used in gene therapy to deliver therapeutic drugs to targeted areas.

While electrical stimulation and targeted drug delivery have enabled more accurate and better treatment for a number of medical conditions, the ability to monitor and detect the physiological and chemical environment surrounding implanted probes has been limited. For example, in continuous glucose sensing and injection therapy, the sensing probe is designed for glucose only and with a limited lifetime. Moreover, it does not sense any other blood chemicals and requires replacement every couple of days. In gene therapy, magnetic imaging and/or ultrasound imaging can monitor the treatment progress, but they usually require visits to facilities having the necessary imaging equipment and do not provide real time tissue and chemical information.

SUMMARY

Principles of the present disclosure provide probe assembly fabrication processes and techniques for obtaining real time chemical information using Raman spectroscopy in vivo, in either steady state detection or in conjunction with electrical stimulation and in physiological signaling (ion channel activation).

An exemplary method includes obtaining a probe assembly including a probe housing, a cavity extending through the probe housing, a plurality of optical fibers within the probe housing, and a probe housing surface adjoining the cavity and configured for enhancing Raman spectroscopy. The probe assembly is positioned within body tissue. Monochromatic light having a first wavelength is emitted by one or more of the optical fibers and towards the probe housing surface configured for enhancing Raman spectroscopy. Surface enhanced Raman scattered light generated within the cavity is conveyed to a detector for spectral analysis of the scattered light via one or more of the optical fibers.

A method of fabricating a probe assembly includes obtaining a distal housing portion including a proximal surface, a pair of opposing projections extending from the proximal surface, and a slot between the pair of opposing projections. A SERS-facilitating assembly including nanorods extending therefrom is also obtained. The SERS-facilitating assembly is positioned within the slot and attached to the distal housing portion. The method further includes connecting a bundle of optical fibers to the distal housing portion such that one or more of the optical fibers are in opposing relation to the SERS-facilitating assembly and at least a first optical fiber within the bundle of optical fibers is positioned for emitting light into the slot in the direction of the SERS-facilitating assembly and at least a second optical fiber within the bundle of optical fibers is positioned for receiving light scattered near the SERS-facilitating assembly.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed.

Substantial beneficial technical effects are provided. For example, one or more embodiments may provide one or more of the following advantages:

Trace chemical sensing;
Facilitating cell stimulation;
Enhancing diagnostic and monitoring capability in vivo;
Deep tissue sensing and stimulation;
Ion channel investigation;
Surface-enhanced Raman (including Terahertz-Raman) spectroscopy.

These and other features and advantages of the present invention will become apparent from the following detailed description of illustrative embodiments thereof, which is to be read in connection with the accompanying drawings.

BRIEF DESCRIPTION OF THE DRAWINGS

The following detailed description, given by way of example, will best be appreciated in conjunction with the accompanying drawings, in which:

FIGS. 3A-3F include a flow diagram showing fabrication of an exemplary probe assembly including the optical fiber bundle;

FIG. 6A is a schematic, cross-sectional view showing an exemplary probe assembly in accordance with a first alternative embodiment;

FIG. 6B is a schematic, cross-sectional view showing an exemplary probe assembly in accordance with a second alternative embodiment, and FIG. 6C is a schematic, cross-sectional view showing an exemplary probe assembly in accordance with a third alternative embodiment.

DETAILED DESCRIPTION

Principles of the present disclosure will be described herein in the context of illustrative embodiments. It is to be appreciated, however, that the specific embodiments and/or methods illustratively shown and described herein are to be considered exemplary as opposed to limiting. Moreover, it will become apparent to those skilled in the art given the teachings herein that numerous modifications can be made to the embodiments shown that are within the scope of the claims. That is, no limitations with respect to the embodiments shown and described herein are intended or should be inferred.

Figure 1:
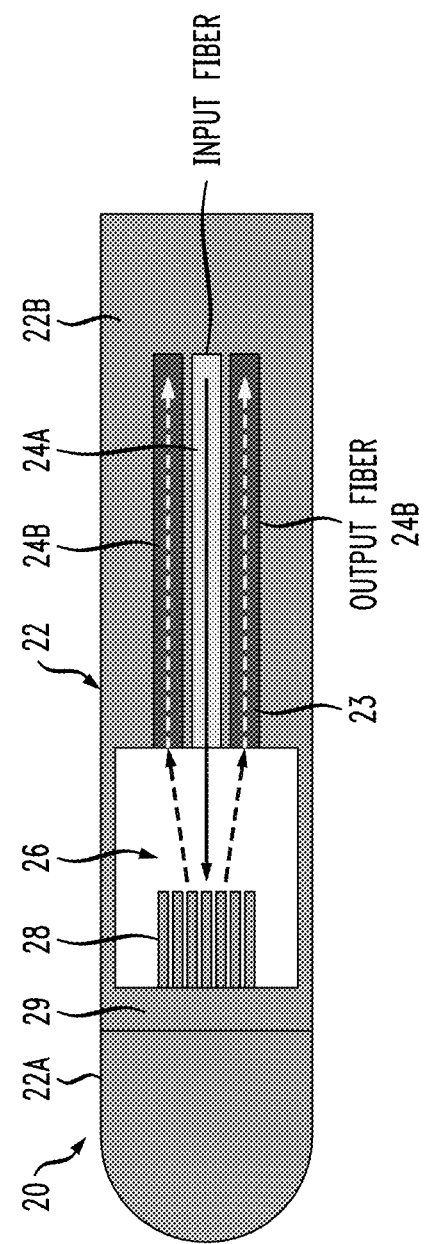
FIG. 1 is a schematic, cross-sectional view showing an exemplary probe assembly.

FIG. 1 schematically illustrates a probe assembly 20 for deep implant in vivo chemical sensing and optionally tissue stimulation. It will be appreciated that the probe assembly 20 may also be usable in some in vitro applications. An exemplary probe assembly 20 includes a needle-shaped housing 22 including distal and proximal end portions 22A, 22B. The housing 22 is made from platinum (Pt), Pt-BMG or any material that is bio-compatible with the tissue in which it is to be implanted. The exemplary housing has a cylindrical configuration with a hemispherical distal end. The proximal end portion 22B of the probe assembly includes embedded optical fibers within a cylindrical housing portion. One or more of the fibers are input fibers 24A that are optically connected to a laser source (not shown). The input fibers 24A are coupled to a lens that focuses light at a selected target, as discussed further below. A gradient index (GRIN) lens is preferred. Gradient index lenses are commercially available. Grintech GmbH, for example, provides GRIN lenses for applications in the field of neuroscience. Other fiber(s) are return fibers 24B that are optically connected to a laser spectrometer (not shown). In some embodiments, the optical fibers 24A, 24B are incorporated within a bundle of single mode (monomode) fibers, each fiber having a core diameter of about eight to ten microns (8-10 μm). The use of single mode fibers enables miniaturization of the probe assembly 20. A GRIN lens may be employed to focus the scattered light, which carries chemical information, prior to entry within the return fibers 24B. The diameter of the probe assembly 20 is between 0.1 mm and 2.5 mm in some embodiments. Probes employed for deep brain stimulation (DBS) typically have diameters of about 1.25 mm. In embodiments that allow the use of larger probe assemblies, bundles of multi-mode fibers may be feasible. Some embodiments may include graded index optical fibers. The bundle, which includes seven or more fibers in one or more embodiments, is branched into the input and output (return) fibers.

As further shown in FIG. 1, the probe housing 22 includes a cavity 26 or "eye" extending laterally with respect to the longitudinal axis of the probe housing. The exemplary probe assembly 20 accordingly resembles a blunt-ended needle having an eye extending through a distal region thereof. The optical fibers in the exemplary probe assembly 20 have ends that terminate at the proximal side of the cavity 26. Each fiber end can be a straight terminated optical surface. The input fiber(s) may include a micro lens or ball(s) as needed to direct the light towards the target or, as discussed above, is operatively associated with a GRIN lens to focus the light on the target. In some embodiments, an input fiber 24A includes a distal end portion that is centrally located and substantially coaxial with the longitudinal axis of the probe assembly. The distal end portion of the input fiber or fiber bundle may comprise a lens. The distal end of the input fiber 24A adjoins the cavity 26 and is in opposing relation to the probe surface that bounds the distal end of the cavity and facilitates SERS. As discussed further below, other input fibers can be targeted away from the SERS-facilitating surface to enable light stimulation of body tissue adjoining the probe assembly, such targeting being facilitated by a lens in one or more embodiments. The laser source accordingly has multiple targets in some embodiments that are selectable from the input fibers 24A. The distal ends of the output fibers 24B adjoin the same end of the cavity 26 as the input fiber(s) and form a generally circular array surrounding the end of the input fiber(s) in some embodiments. The light from a laser source (not shown in FIG. 1) may pass through a band pass filter (such as a reflecting Bragg grating (RBG) BragGrate™ band pass filter available, for example, from OptiGrate Corp.) prior to entering the input fiber 24A. The light scattered within the cavity 26, schematically illustrated by arrows including broken lines in FIG. 1, may pass through a notch filter (not shown) such as a BragGrate™ Notch Filter (BNF) intended for ultra-low-frequency Raman spectroscopy. Such a notch filter is available from Optigrate, Inc. and is employed prior to the light entering a spectrometer for analysis. Both the input band pass filter and the notch filter are incorporated within the probe housing in some embodiments. The cavity 26 is configured to collect tissue and/or inter-cellular fluid from the area in which it is placed. In embodiments where the probe assembly is maintained in the patient for sufficient time, tissue growth within the cavity is expected.

Figure 4A:
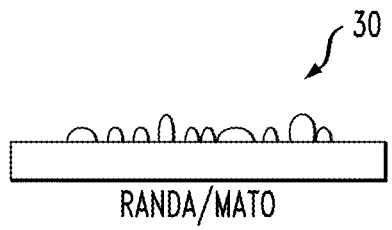
FIGS. 4A and 4B are schematic illustrations of exemplary probe surfaces for facilitating surface-enhanced Raman spectroscopy.
Figure 4B:
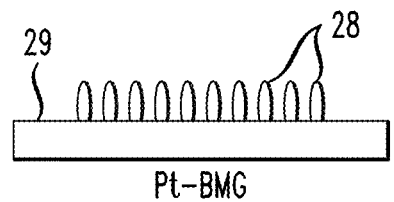

The probe surface opposing the distal ends of the optical fibers 24A, 24B is configured to facilitate surface-enhanced Raman spectroscopy (SERS) with respect to one or more chemical materials of interest. In some embodiments, the surface opposing the distal ends of the optical fibers is comprised of an array of nanorods 28 as schematically illustrated in FIGS. 1 and 3B. The nanorods have sizes and shapes (height, pitch and 2D grids patterns, or random patterns) chosen to facilitate SERS. A plane symmetry group is a mathematical classification of two-dimensional (2D) repetitive patterns, there being seventeen (17) distinct groups. In addition to a random distribution of nanorods, a SERS-facilitating assembly incorporated within the probe assembly 20 may optionally include nanorods in any of the seventeen groups. The nanorods may need to be on a regular grid to match the incident light symmetry. In one exemplary embodiment, a p4 mm symmetry group is employed for square grids. In another embodiment, a p6 mm symmetry is employed for hexagonal close pack (HCP) grids. In a further embodiment, a pmm2 symmetry is employed for rectangular symmetry grids. Bulk metallic glass (BMG) nanorods may be employed, such as platinum-based BMG nanorods having the composition $Pt_{57.5}Cu_{14.7}Ni_{5.3}P_{22.5}$. Such nanorods have dimensions, densities (spacing), orientations and aspect ratios that can be chosen based on the molecule(s) to be detected and analyzed. Exemplary Pt-BMG nanorods have diameters between five and five hundred nanometers (5-500 nm), aspect ratios (nanorod lengths/diameters) between one and ten, and average spacing between two and ten times nanorod diameter. Nanorods having diameters of less than 200 nm are preferred in some exemplary embodiments. Nanorods having diameters of about one hundred nanometers may, for example, have heights of about one micron in some embodiments. Aspect ratios can be greater than ten in some embodiments. Nanorod heights in an array may or may not be equal. In some exemplary embodiments, nanorod density is between $(0.4$ to $40) \times 10^9$ nanorods/cm$^2$ (this corresponds to 500 nm to 50 nm pitch grids) and nanorod length is one micron or greater. The Pt-BMG nanorods can be coated with gold or silver nanoparticles to provide additional signal enhancement, though such coatings are not required as Pt-BMG nanorods facilitate SERS without any coatings for at least some molecules such as glucose. Nanorods formed from other materials, such as zinc oxide (ZnO), do not effectively facilitate SERS and accordingly should be coated with a metal such as silver. Pt-BMG nanorods can be fabricated by placing a Pt-BMG alloy plate on a preheated alumina nanoporous mold located between planarized metal plates. Upon the application of a compressive force via the planarized plates above the glass transition temperature of the alloy, the material begins to flow and enters the nanopores on the exposed mold surface. While the Pt-BMG remains in an amorphous state above the glass transition temperature, the applied compressive force is incrementally increased to a maximum threshold ranging from 25-50 kN dependent on the nanorod diameter to be obtained. The duration of processing time above the glass transition temperature is about seven minutes to prevent crystallization of the Pt-BMG. The nanopatterned area of the Pt-BMG substrate continues to increase radially in diameter during the process. Once the desired substrate has been obtained, the alumina mold is dissolved in a potassium hydroxide solution. The finished substrate includes a base 29 having nanorods 28 extending therefrom, as schematically illustrated in FIGS. 1 and 4B. The nanorod density values are equivalent to the pore density of the alumina mold. The mold may include cylindrical nanopores for the production of cylindrical nanorods. Other nanopore configurations can alternatively be employed to form, for example, nanorods having triangular, semicircular, trapezoidal, or rectangular cross-sections. Combinations of differently shaped nanorods are formed in some embodiments. The nanorod pattern on the base is also determined by the pattern of nanopores within the mold. The nanorods may be formed, for example, in a rectangular or hexagonal pattern. Combinations of patterns are also feasible.

While the nanorods are shown as extending generally parallel to the longitudinal axis of the probe and cavity in FIG. 1, they may alternatively extend radially with respect to the longitudinal axis or at other orientations for some applications. The base 29 from which the nanorods extend has a proximally facing planar surface in some embodiments. In other embodiments, the base 29 includes a concave surface facing the distal ends of the optical fibers that facilitates focusing of the light within the cavity 26 and light collection efficiency. The probe surface opposing the distal ends of the optical fibers 24A, 24B may be comprised of materials other than Pt-BMG and structures other than nanorods that facilitate SERS. Gold and silver surfaces including bio-compatible materials are among the possible options. Metal (e.g. silver) nanoparticles in certain size ranges are employable as SERS substrates. Randa and Mato substrates 30, as schematically illustrated in FIG. 4A, are a further option for incorporation within the probe assembly 20. Such substrates are commercially available and can be cut to appropriate size for attachment to the probe housing. Substrates including gold or silver deposited on soda-lime glass can provide Raman signal enhancement. As schematically illustrated in FIG. 4A, the nanopattern on the substrate surface includes features having a variety of sizes ranging, for example, from tens of nanometers to hundreds of nanometers to which analyte molecules (not shown) may be attached when the probe assembly 20 is in use. Feature sizes are less than one hundred nanometers (100 nm) in some embodiments. Coatings of gold or silver particles that are also less than one hundred nanometers (100 nm) in average diameter facilitate a strong surface plasmon response. (Other possible coatings include, but are not necessarily limited to, platinum and titanium dioxide ($TiO_2$)). An analyte molecule in the vicinity of an effective plasmonic surface is characterized by increased absorption of the emitted light and an increased Raman signal.

The distance between the probe surface 23 including the distal fiber ends adjoining the cavity 26 and the opposing probe (SERS-facilitating) surface is in a range of about one hundred to two thousand microns (100 μm to 2,000 μm) in some exemplary embodiments. This distance may be variable depending on the dimension(s) of the surface features of the SERS-facilitating surface. The SERS-facilitating assembly 28, 29 of the SERS-facilitating surface is hydrophilic in some embodiments. Other probe housing surfaces, including the surfaces bounding the cavity 26, are also hydrophilic in some embodiments. Such hydrophilic cavity surfaces may facilitate detection of some analytes. Hydrophilic probe housing surfaces can be obtained using conventional processes such as low pressure plasma surface treatment or subjecting the surfaces to acid(s) to slightly dissolve the surface material. Pt-BMG nanorods are hydrophobic, but can be processed in such a manner to render them hydrophilic. In some embodiments, hydrophobic Pt-BMG nanorods are employed within the probe assembly.

Figure 2A:
FIGS. 2A-2D include a flow diagram showing fabrication of an exemplary optical fiber bundle.
Figure 2B:
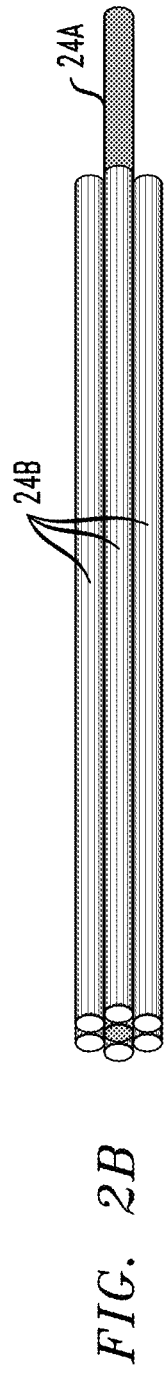
Figure 2C:
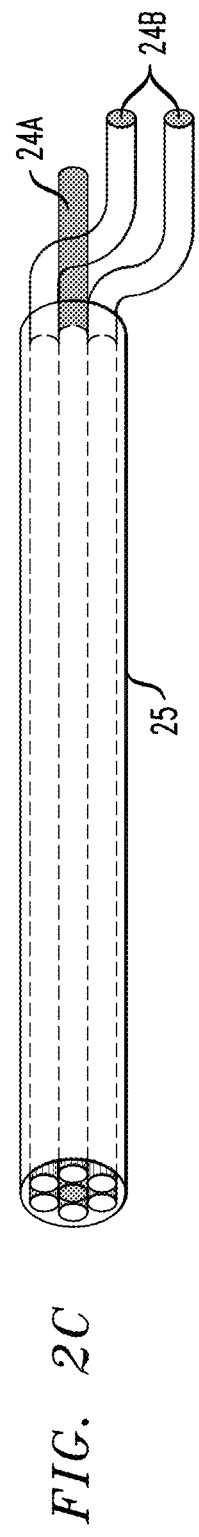
Figure 2D:
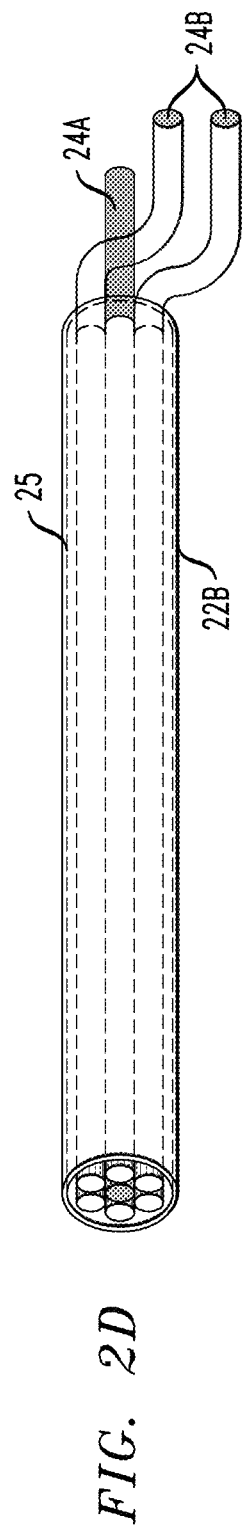

An exemplary fabrication process for obtaining a probe assembly 20 as described above is described with reference to FIGS. 2A-2D and 3A-3F. FIG. 2A shows an input fiber 24A while FIG. 2B shows a fiber bundle including an array of six output fibers 24B positioned about the circumference of the input fiber 24A. The output fibers 24B accordingly form a circular configuration in the portions to be positioned within the probe housing 22. The portions of the fibers 24B extending outside the probe housing may be stacked on top of each other or in other suitable configuration(s) to facilitate connection to the spectrometer employed. The distal ends of the optical fibers 24A, 24B are polished and coplanar in some embodiments. Both the input and output fibers are operatively associated with lenses such as GRIN lenses in exemplary embodiments. As discussed above, the fibers can be monomode fibers to allow small probe dimensions (for spectroscopic requirement to reduce light dispersion.) In some embodiments, the casing 25 is extruded. An biocompatible coating material such as parylene may comprise the outer surface of the casing 25. The encased fiber bundle is positioned within a cylindrical housing that later forms the proximal end portion 22B of the probe housing as shown in FIG. 1. A Pt-BMG housing having the composition $Pt_{57.5}Cu_{14.7}Ni_{5.3}P_{22.5}$ is employed in some embodiments. Other bio-compatible housing materials include platinum, glass, and titanium. The selection of housing materials and coatings thereon depend in part on the intended application of the probe assembly.

The distal end portion 22A of the housing may also be formed from Pt-BMG having the same composition as the proximal end portion thereof. Other materials, such as those identified above with respect to the proximal end portion 22B of the housing, may alternatively be employed. As schematically illustrated in FIG. 3A, a substrate 50 having a hemispherical distal end and a cylindrical body is cast from Pt-BMG, glass, titanium or other suitable material, possibly further including a conformal coating of parylene or other suitable material for biocompatibility. The diameter of the cylindrical body and the proximal end portion 22B of the probe assembly are the same in some embodiments. A slot 51 is formed in the cylindrical body, leaving a pair of projections 52 having opposing flat surfaces and a proximally facing surface 53 from which the projections 52 extend. A laser cutter may be employed to form the slot 51. In some embodiments, the surface 53 is concave to facilitate reflection from the SERS-enhancing later formed thereon or secured thereto. The surface 53 is planar in other embodiments. A SERS-facilitating assembly is cut to size and secured to the proximally facing surface 53. As discussed above, the SERS-facilitating assembly may include a base 29 having nanorods 28 extending therefrom. Such SERS-facilitating assemblies can be fabricated from Pt-BMG using the process described above and cutting (dicing) the resulting structure to obtain SERS-facilitating assemblies sized to fit within the distal end portion 22A of the probe housing, as shown in FIG. 3C. The base of the assembly is laser welded to the distal end portion of the probe housing to obtain the structure 54 shown in FIG. 3D. The nanorods 28 in some embodiments extend parallel to the longitudinal axis of the probe assembly 20. (The nanorods 28 are greatly enlarged in FIGS. 3C and 3D for purposes of illustration.) As further discussed above, other types of SERS-facilitating structures can instead be incorporated within the probe assembly. The structure 54 including the SERS-facilitating assembly is aligned with the pre-assembled proximal end portion 22B of the probe housing that contains the fiber bundle. As shown in FIG. 3E, the longitudinal axes of the two structures are aligned such that the nanorods are in opposing relation to the distal ends of the optical fibers 24A, 24B. The housing portions 22A, 22B are joined by laser welding or other suitable process to obtain the probe assembly 20 shown in FIG. 3F. In the exemplary process, the ends of the projections 52 are welded to the end surface of the proximal housing portion 22B so that a cavity 26 extends through the probe assembly and laterally with respect to the longitudinal axis of the probe assembly. The length of the slot 51 is the same as the length of the cavity 26 within the probe assembly formed upon attachment of the housing portions 22A, 22B to each other. The resulting probe assembly may be cleaned and polished prior to use.

Referring again to FIGS. 1 and 3F, the positioning of the optical fibers and the opposing probe surface facilitate the detection of molecules as well as light collection, enabling trace chemical analysis in tissue and body fluids such as blood. The dimensions of the cavity 26, the substrate used for attaching analyte molecules, and the wavelength of the light entering the cavity are among the variables tailored for specific applications. A laser source for performing SERS may, for example, be employed for providing 532 nm (green), 632 nm (red), 785 nm (NIR), 1032 nm, or other wavelengths. Terahertz (THz) radiation can alternatively be emitted into the cavity 26 using solid state lasers. A Terahertz-Raman spectroscope, incorporating a BragGrate™ Notch Filter (BNF) and mono-mode optical fiber bundles, is particularly suitable for some embodiments of the probe assembly where Raman SERS is employed to detect terahertz signatures from macro-molecules such as proteins. Laser wavelength and/or intensity are selected to perform SERS in some applications and for tissue stimulation in other applications of the probe assembly. Deep brain sensing and stimulation are feasible using some embodiments of the probe assembly configured for use in the thalamus or hypothalamus regions. The probe assembly 20 can be employed by introducing it to a selected area that is to be monitored, for example the brain, an intramuscular area, or an organ. Probe assembly implantation can be facilitated by employing a plastic or glass implanter (not shown) that encases the probe assembly during insertion. The implanter is removed to expose the cavity 26 once the probe assembly 20 is properly positioned.

Figure 5:
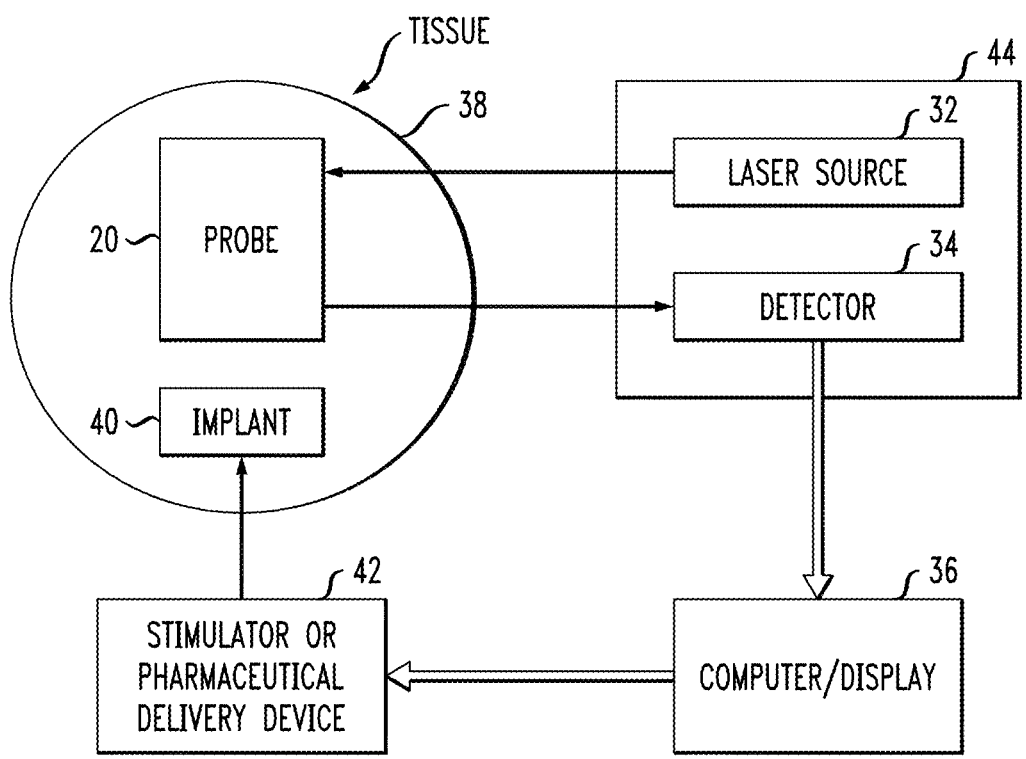
FIG. 5 is a schematic diagram of a system including the exemplary probe assembly.

FIG. 5 shows a system including an exemplary probe assembly 20 used in conjunction with operatively associated devices. The input fiber(s) of the probe assembly are optically connected to a laser source 32 while the output fiber(s) are optically connected to a detector 34 such as a spectrometer. In some embodiments, the laser source is a distributed feedback laser (DFB) such as a quantum cascade laser (QCL). The laser source 32 is an external unit in some embodiments and is integral with the probe assembly 20 in other embodiments. The detector 34 may also be an external unit in some embodiments and integral with the probe assembly in other embodiments. The probe assembly may further include an integrated circuit including an antenna (not shown) electrically connected to the detector for transmitting spectroscopic data wirelessly from the probe assembly. A power supply (not shown) is incorporated within the probe assembly in some embodiments including integral laser sources and antennas. In some embodiments, the spectrometer, laser source and power supply are provided within a housing 44 that is worn by the patient. An optional antenna within the housing 44 allows data from the spectrometer to be obtained wirelessly. A computer 36 having an optional display is operatively associated with the detector 34. In this exemplary use, the probe assembly 20 is implanted within body tissue 38. The probe assembly 20 may be encased within an implanter body (not shown) to protect the cavity 26 until it is positioned at the desired location within the tissue. The cavity 26 is then exposed to allow the admission of inter-cellular fluids and/or tissue therein for subsequent detection using Raman spectroscopy. Chemical sensing can be conducted within or outside cell walls using probe assemblies containing SERS-facilitating structures such as nanorods, as discussed above. An implant 40 is positioned within the tissue 38 in proximity to the probe assembly 20. In some embodiments, the implant 40 comprises a microfluidic catheter and is used for delivering pharmaceutical preparations within a controlled target area. (The microfluidic catheter is also employed for retrieving bodily fluids in some embodiments.) In such embodiments, the implant is connected to a device 42 for causing the catheter to deliver correct doses of medication at precise time(s). In other exemplary embodiments, the implant 40 is configured for providing electrical stimulation to a precise area of the tissue 38. Implants have been developed to provide, for example, deep brain stimulation through the use of an array of electrodes. Positioning of the implant 40 and probe assembly 20 may be facilitated through the use of magnetic resonance imaging (MRI), CT scans, or other techniques. Stylets and insertion cannulas may be used to introduce some implants designed for providing electrical brain stimulation, as known in the art. The implant for providing electrical stimulation is connected to a device 42 such as a pulse generator configured to control the amount and duration of electrical stimulation. The device can be implanted within the body or worn outside the body of the patient. Operation of the device 42 and/or the laser source 32 is controlled by the computer 36 that processes information obtained from the detector 34. Electrical tissue stimulation, light stimulation, and/or drug delivery can be controlled based on real time spectroscopic data obtained using the probe assembly 20. Deep brain laser light stimulation has also been proposed as a technique for treating medical conditions by stimulating cells without damaging or destroying them. The probe assembly 20 discussed herein can be used to provide such laser light stimulation or be used in conjunction with an implant specifically designed for light stimulation or for providing multiple types of cell stimulation. While the probe assembly 20 and implant 40 are shown as individual elements in FIG. 5, they may be arranged as an integral structure in some embodiments.

The exemplary probe assembly 20 shown in FIG. 5 is employed to spectroscopically detect the chemical environment in which the implant 40 operates in real time. It can be further employed to provide laser light stimulation to the surrounding tissue, possibly facilitating drug absorption by the cells in embodiments wherein catheters or other drug-delivery vehicles in proximity to the probe assembly are employed to provide pharmaceutical preparations. Electrical stimulation and/or pharmaceutical delivery can be adjusted based on the spectroscopic information that is obtained from the probe assembly. In some embodiments, such adjustments are based on the detection of trace neurotransmitter chemical materials. The chemical information obtained can be used as a basis for adjusting the timing and/or dosage of pharmaceutical delivery to the tissue adjoining the implant 40 and probe assembly 20 and/or to indicate the need for stimulating the tissue through laser light emission(s) of an appropriate wavelength. The probe assembly 20 allows monitoring of chemical activities in vivo using SERS and, in at least some embodiments, activating cellular channels if the healing process reduces the amount of plasma fluids in an area of interest. The SERS-facilitating surface of the probe assembly and the wavelength of the light transmitted into the probe cavity 26 are selected to enhance detection of chemicals of interest. Biological targets such as insulin, lysozyme, and dopamine are sensitive to infrared (IR) or near-IR light (785 nm). Live tissue applications may involve the exposure of membrane proteins such as sodium channels or G proteins to laser light emitted by the probe assembly. When the probe assembly is employed for cell stimulation, the laser wavelength is selected to affect only the molecules of interest. In embodiments where nanorods are employed to facilitate SERS, they also provide physical anchoring within the body tissue 38 as cells grow within the cavity 26. Nanorod spacing (pitch) in the range of 100-200 nm can inhibit foreign body rejection and help avoid foreign body rejection of the probe assembly due to "body heal." Nanorod lengths exceeding one micron facilitate such multi-purpose functionality, and nanorod lengths of one to ten microns are preferable in at least some applications such as where chemical sensing both within and outside cell walls is desired. Light activation of cell wall channels may facilitate nanorod positioning through cell walls.

Probe assemblies as described above can be employed for use within brain tissue, muscles, and other human/animal organs for chemical detection and/or stimulation. They can alternatively be employed within plant tissue or in non-living structures for trace chemical detection. In some in vivo uses, the probe assembly 20 is positioned within body tissue such as brain tissue where it remains in place for a sufficient time for intercellular fluids to move within the cavity 26 and/or for cell growth to penetrate the cavity. An implant 40 may or may not be positioned within the body tissue at the same time as the probe assembly. The laser source is activated to cause light to be emitted from the input fiber(s) 24A. The wavelength of the emitted light and optical power are selected in some instances to stimulate tissue surrounding the cavity. Light stimulation of deep tissue is feasible using the probe assembly 20 as described above or including additional input fibers specifically intended for tissue stimulation as opposed to SERS.

In embodiments of the probe assembly where tissue light stimulation in addition to surface enhanced Raman spectroscopy is to be provided, the SERS area 28 and SERS base 29 (with nano-rods or other structures) are relatively small (100 µm×100 µm or less, to maintain a good spectroscopic accuracy. (FIG. 3C shows an exemplary structure including such elements 28, 29 prior to incorporation within a distal housing portion 22A.) The total distal base area defined by the proximally facing surface 53 is about 1 mm×1 mm in an exemplary structure, much larger than the SERS area and associated base 29. (The figures are not drawn to scale.) Some of the incident fibers 24A (or, with reference to FIG. 6C, 124A) (10-50 µm in diameter) are arranged to direct light to the distal area 53 outside of the SERS area 28, 29. The probe assembly is configured for focusing light emitted by the fibers to selected targets, which include the SERS elements 28, 29 and optionally an area displaced from the SERS elements. As known in the art, gradient index (GRIN) lenses can be paired with optical fibers for focusing light. Commercially available assemblies that may be employed in some embodiments include sleeves for receiving GRIN lenses through one end and a pigtailed ferrule including one or more optical fibers into the opposite end. Thorlabs Inc., Newton, N.J. is among the manufacturers of such assemblies. If the distal housing portion 22A is transparent to the light emitted by the input fibers, light emanating from the housing portion 22A can be used to scatter the light into the tissues where the hemispherically shaped end and optional texturing will assist the light scattering. The stimulation laser can be the same SERS laser 32 but uses fiber bundles that are not focused on the SERS area 28,29. As parylene is transparent, the coating of the distal housing portion 22A with such a polymer does not inhibit light stimulation of the surrounding tissue.

FIG. 6C shows an exemplary probe assembly 20C configured for facilitating SERS and providing light stimulation of nearby tissue. The same reference numerals are employed in this figure to designate elements that are the same or substantially similar to those found in the preceding figures. Two input fibers 24A, 124A are incorporated within the proximal housing portion 22B of the probe assembly 20C and are positioned for emitting light into the slot 26 and towards the distal housing portion 22A. The first input fiber 24A (or bundle of input fibers) is positioned to cause Raman scattering by molecules interacting with the area configured for enhancing SERS, for example nanorods 28. A GRIN lens is preferably coupled to the input fiber or fiber bundle to focus the light on the SERS-enhancing area. Reflected light is gathered by output fibers, which are not shown in this figure. The second input fiber 124A is arranged to direct light to an area 29A forming a transmission target outside the area configured for enhancing SERS. A GRIN lens may be provided for focusing light from the second input fiber or fiber bundle. In some embodiments, this area 29A includes an anti-reflective (AR) coating, the choice of which depends on the wavelength of the light to be emitted by the input fiber 124A to cause tissue stimulation. An anti-reflective coating is also provided on the outer surface of the distal housing portion 22A in some embodiments. As discussed above, the area occupied by the SERS-facilitating assembly is much smaller than the area of the proximally-facing end surface of the distal housing portion 22A in some embodiments, facilitating the dual purpose of the exemplary probe assembly 20C of providing light stimulation of surrounding tissue and obtaining chemical information from light scattered by molecules interacting with the SERS-facilitating assembly. The distal housing portion 22A of the exemplary probe assembly 20C is transparent (e.g. glass) so that light 124B emitted by the second input fiber 124A escapes the probe assembly. In some embodiments, the distal end of the distal housing portion 22A is both spherical and textured. The housing surface may itself have a rough, textured surface to enhance light scattering or a transparent coating thereon may instead have a textured surface.

In some embodiments, the wavelength and/or optical power are chosen to facilitate the detection of materials, for example proteins or enzymes, within the cavity 26. In the latter case, signals obtained are enhanced by the interaction of the detected material with the probe surface (e.g. BMG nanorods) opposing the input fiber(s), enabling SERS. In some embodiments, the probe assembly 20 is employed to determine the efficacy of laser light stimulation by spectroscopically determining whether or not the adjoining, light-stimulated cells have produced targeted materials. As discussed above, the probe assembly 20 is employed in conjunction with an implant 40 in some embodiments. The implant and probe assembly are positioned within several millimeters of each other in some applications. If both are positioned in selected brain tissue, such as a targeted region of the subthalamus, the efficacy of various types of treatments on the production of neurotransmitters such as dopamine can be detected. Such treatments may include laser light stimulation and/or electrical stimulation. Light and/or electrical stimulation of the body tissue is performed by the probe assembly itself in some embodiments rather than an adjoining implant. In embodiments wherein the implant 40 includes a catheter for delivering pharmaceutical preparations, the SERS enabled by the probe assembly may help determine the effects of such preparations on the surrounding tissue in real time.

FIGS. 6A and 6B schematically illustrate two further exemplary probe assemblies 20A, 20B. Both probe assemblies are configured for enabling SERS as well as the electrical stimulation of tissue. The same reference numerals are employed in these figures to designate elements that are the same or substantially similar to those found in the preceding figures. The probe assembly depicted in FIG. 6A is similar to that shown in FIG. 1 in that it includes a surface for enhancing Raman spectroscopy near the distal end of the probe housing 22. While nanorods 28 are provided in the exemplary structure, other materials and types of surfaces can be alternatively employed. Nanorods having an aspect ratio (height to diameter) between one and ten and a pitch ratio (ratio of diameter to distance between nanorods) of two to ten are employed in some embodiments. A pitch ratio of three or less is used in some embodiments as cells will tend to stay on the surfaces of the nano-rods. The chemicals sensed in such embodiments are mostly extracellular molecules. In other embodiments, the pitch ratio is four or more such that the nano-rods tend to become embedded into the cells and therefore detect inter-cellular chemicals. The surface can comprise Pt-BMG, Au, Ag, $TiO_2$ or other materials that facilitate SERS. A slot 26 near the distal end of the probe assembly 20A forms a light cavity. The input and output fibers 24A, 24B adjoin the light cavity. Light emitted by the output fiber(s) is targeted at the SERS-facilitating surface (e.g. nanorods 28) while the output fibers are configured to receive light scattered by molecule(s) interacting with the SERS-facilitating surface. Input fibers may further be targeted away from the SERS-facilitating surface for the purpose of providing light stimulation to surrounding tissue. As described above, the distal end portion 22A of the housing may be transparent if the probe assembly is intended to further provide light stimulation. A plurality of electrodes 21 are attached to the outer surface of the proximal portion 22B of the probe housing 22. The electrodes may be in the form of a plurality of metal rings located proximal to the light cavity. In some embodiments, an electrode can completely encircle the probe housing in order to provide omnidirectional tissue stimulation. In other embodiments, the electrode comprises several ring segments that facilitate directional stimulation. Unipolar and bipolar deep brain stimulation using the electrodes are also feasible in some embodiments. Unipolar stimulation is provided when all of the electrodes are activated at the same time. Bipolar stimulation, wherein one electrode contact functions as an anode while another functions as a cathode, generally produces a more focused area of tissue stimulation than is obtained using unipolar stimulation. The electrodes 21 are electrically connected to a device such as a pulse generator. Amplitude, frequency and length (pulse-width) of stimulation can be selected and/or adjusted depending on the condition being treated and/or detected treatment results. The configuration of the probe assembly 20A may accordingly enable light stimulation of surrounding tissue, electrical stimulation of surrounding tissue, and detection of molecules interacting with the SERS-facilitating surface (e.g. nanorods 28). In some embodiments, a laser source including an ultranarrow-band notch filter is employed in conjunction with a mono-mode input fiber 24A in the probe assembly 6A for terahertz-Raman spectroscopy. Notch filters including volume holographic gratings have been developed for facilitating terahertz-Raman spectroscopy.

The probe assembly 20B shown in FIG. 6B includes electrodes 21 located distally of the slot that forms the light cavity 26. The probe housing includes a cylindrical distal end portion 122A which supports the ring-shaped electrodes 21. One end of the distal end portion is formed as a hemisphere. The opposite end 25, which is integral with the distal end portion 122A in some embodiments, includes a pair of projections similar to those described with respect to FIG. 3B. A light cavity is formed by a slot 26 between the two projections. The proximal end portion 122B of the probe assembly housing is cylindrical and contains the input and output fibers 24A, 24B. SERS-facilitating structure(s) such as nanorods 28 are incorporated within the light cavity and positioned to receive light emitted by the input fiber(s). The output fibers 24B are positioned to receive light scattered by molecules interacting with the SERS-facilitating structures. The dimensions of the probe assemblies 20A and 20B may be about the same as those described above with respect to the probe assembly 20. All of the disclosed probe assemblies 20, 20A, 20B and 20C can be employed for terahertz-Raman spectroscopy.

Given the discussion thus far, an exemplary method for obtaining chemical data includes obtaining a probe assembly 20 including a probe housing 22, a cavity 26 extending through the probe housing, a plurality of optical fibers 24A, 24B within the probe housing, and a probe housing surface adjoining the cavity and configured for enhancing Raman spectroscopy. FIGS. 4A and 4B illustrate exemplary distal probe housing surfaces configured for SERS. The probe assembly is positioned within body tissue 38, as schematically illustrated in FIG. 5. Monochromatic light having a first wavelength is emitted by one or more of the optical fibers 24A and towards the distal probe housing surface adjoining the cavity 26. Surface enhanced Raman scattered light generated within the cavity 26 is conveyed to a detector 34 for spectral analysis of the scattered light via one or more of the optical fibers 24B. Portable Raman detector systems are employed in some embodiments. Such detectors are commercially available. In some embodiments, the probe assembly further includes a gradient index lens operatively associated with the one or more of the optical fibers for focusing the monochromatic light on the probe housing surface configured for enhancing Raman spectroscopy. The distal probe housing surface adjoining the cavity 26 includes BMG nanorods 28 in some embodiments such as Pt-BMG nanorods. In some embodiments, the BMG nanorods are caused to be positioned both within and outside cell walls within the body tissue. Accordingly, chemical sensing can be made both within and outside the cell walls in some embodiments. The extension of the nanorods through cell walls is caused by cell diffusion towards the cavity and by using light activation of the cell wall channels. Such light activation is provided in some embodiments by the emission of laser light of a selected wavelength by the input fiber(s), such as described above with reference to FIG. 6C. The wavelength and optical power of the light emitted for light activation may or may not be the same as those used for chemical analysis using the SERS technique. Some embodiments of the method include introducing a catheter or an electrical stimulator within the body tissue in proximity to the probe assembly 20. In embodiments including a catheter, a pharmaceutical preparation is introduced into the body tissue through the distal end of the catheter and the detector is used to determine an effect of the pharmaceutical preparation on the body tissue proximate to the probe assembly. The pharmaceutical delivery system may alternatively or additionally retrieve bodily fluid for external chemical analysis.

In embodiments wherein electrical stimulation of body tissue near the probe assembly is to be provided, the body tissue is subjected to electrical stimulation using either an implant or electrodes 21 mounted to the probe assembly and the detector is used to determine an effect of the electrical stimulation on the body tissue. In vivo determination of the effects of light and/or electrical stimulation and of pharmaceutical preparations is facilitated by the probe assembly. In some embodiments, both the input and scattered light are within the terahertz spectrum. In some other embodiments, the input and scattered light are in the infrared (IR) range, but the system is configured for resolving chemical signatures in the terahertz region ("IR carried terahertz"). The laser source and spectrometer both operate in the visible and IR regions in some embodiments, and both can operate in the terahertz range in some embodiments. In one or more embodiments, the laser source produces light in the visible and IR ranges while the spectrometer is configured for providing chemical signatures in the visible, IR and terahertz regions.

An exemplary assembly for detecting chemical materials using surface-enhanced Raman spectroscopy includes an elongate, implantable probe housing 22 having a proximal end portion 22B, a distal end portion 22A, and a longitudinal axis extending through the proximal and distal end portions of the housing. A cavity 26 extends through the housing and laterally with respect to the longitudinal axis. In some embodiments, the cavity 26 extends through the distal end portion 22A of the housing. A first surface of the distal end portion 22A bounds the cavity 26 and is configured for enhancing Raman spectroscopy. As discussed above, the first surface may include structures as shown in FIGS. 4A and 4B or other structures that facilitate SERS. The proximal end portion of the housing 22 includes a second surface 23 bounding the cavity and in opposing relation to the first surface. A plurality of optical fibers 24A, 24B extends through the proximal end portion 22B of the housing, at least a first one 24A of the optical fibers being positioned for emitting light into the cavity and at least a second one 24B of the optical fibers being positioned for receiving light scattered near the first surface (the SERS-facilitating region) of the distal end portion 22A of the housing. In some embodiments, the assembly further includes a laser source 32 optically connected to the first one 24A of the optical fibers. The assembly may further include a detector 34 for conducting spectral analysis of scattered light optically connected to at least the second one 24B of the optical fibers. The first surface of the distal end portion 22A of the housing comprises hydrophilic bulk metallic glass nanorods 28 in some embodiments, such as Pt-BMG nanorods. The nanorods are at least one micron in length in some embodiments. The nanorods adjoin a base 29 having a planar surface in some embodiments and a concave surface facing the cavity 26 in other embodiments. The first (SERS-facilitating) surface of the distal end portion of the housing bounding the cavity 26 and the second surface 23 of the proximal end portion bounding the cavity are between about one hundred and two thousand microns from each other in some embodiments. As discussed herein, the SERS-facilitating surface may include nanorods or other non-planar surface features such as schematically illustrated in FIGS. 4A and 4B; the distance between the surface 23 and the SERS-facilitating surface is accordingly in a range. The optical fibers are monomode fibers in some embodiments to facilitate miniaturization.

An exemplary system is further provided for obtaining spectroscopic data and using such data to control light stimulation, electrical stimulation, and/or drug delivery within body tissue. The system includes an assembly including an elongate, implantable probe housing having a proximal end portion, a distal end portion, and a longitudinal axis extending through the proximal and distal end portions of the housing. A cavity 26 extends through the distal end portion of the housing in some embodiments and laterally with respect to the longitudinal axis thereof, the distal end portion of the housing including a first surface bounding the cavity and configured for enhancing Raman spectroscopy. FIGS. 4A and 4B show exemplary structures that form the first surface in some embodiments. The proximal end portion including a second surface 23 bounding the cavity and in opposing relation to the first surface. A plurality of optical fibers extends through the proximal end portion of the housing, at least a first one 24A of the optical fibers being positioned for emitting light into the cavity and at least a second one 24B of the optical fibers being positioned for receiving light scattered near the first surface of the distal end portion of the housing. The system may further include an implant proximal to the assembly, the implant configured for providing at least one of electrical body tissue stimulation, light stimulation, and pharmaceutical delivery. As discussed above, electrical stimulation is provided by electrodes on the probe housing in some embodiments. A detector for processing scattered light is optically connected to at least the second one 24B of the optical fibers. The system can be adapted for covering spectrum ranges from visible light to millimeter wavelengths to obtain spectroscopic data.

A method of fabricating a probe assembly for chemical sensing is further provided. Such a method includes obtaining a distal housing portion including a proximal surface 53, a pair of opposing projections 52 extending from the proximal surface, and a slot 51 between the pair of opposing projections. FIG. 3B shows an exemplary distal housing portion, it being appreciated that the length of the distal housing portion is greater in some embodiments such as that shown in FIG. 6B. A SERS-facilitating assembly including nanorods 28 is positioned within the slot 51 and attached (e.g. welded) to the distal housing portion. A bundle of optical fibers is connected to the distal housing portion such that one or more of the optical fibers are in opposing relation to the SERS-facilitating assembly and at least a first optical fiber 24A within the bundle of optical fibers is positioned for emitting light into the slot, targeting the SERS-facilitating assembly. An optically coupled lens facilitates such targeting in some embodiments; the optical fiber 24A as shown is understood as incorporating a lens in one or more embodiments. At least a second optical fiber 24B within the bundle of optical fibers is positioned for receiving light scattered near the SERS-facilitating assembly. In one or more embodiments, obtaining the distal housing portion includes obtaining a substrate including a cylindrical body having distal and proximal end portions, the distal end portion being hemispherical. An exemplary substrate is shown in FIG. 3A. The slot 51 is formed in the proximal end portion of the cylindrical body.

The illustrations of embodiments described herein are intended to provide a general understanding of the various embodiments, and they are not intended to serve as a complete description of all the elements and features of apparatus and systems that might make use of the assemblies and techniques described herein. Many other embodiments will become apparent to those skilled in the art given the teachings herein; other embodiments are utilized and derived therefrom, such that structural and logical substitutions and changes can be made without departing from the scope of this disclosure. It should also be noted that, in some alternative implementations, some of the steps of the exemplary methods may occur out of the order noted in the specification and/or figures. For example, two steps shown in succession may, in fact, be executed substantially concurrently, or certain steps may sometimes be executed in the reverse order, depending upon the functionality involved. The drawings are also merely representational and are not drawn to scale. Accordingly, the specification and drawings are to be regarded in an illustrative rather than a restrictive sense.

Embodiments are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of any means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit thereof. The embodiments were chosen and described in order to best explain principles and practical applications, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, the claimed subject matter may lie in less than all features of a single embodiment. Thus the following claims are hereby incorporated into the Detailed Description, with each claim standing on its own as separately claimed subject matter.

Given the teachings provided herein, one of ordinary skill in the art will be able to contemplate other implementations and applications of the techniques and disclosed embodiments. Although illustrative embodiments have been described herein with reference to the accompanying drawings, it is to be understood that illustrative embodiments are not limited to those precise embodiments, and that various other changes and modifications are made therein by one skilled in the art without departing from the scope of the appended claims.

What is claimed is:

1. A method comprising:
    obtaining a probe assembly including a needle-shaped probe housing, a cavity extending laterally through the probe housing, a plurality of optical fibers within the probe housing, and a metal-containing probe surface comprising nanostructures adjoining the cavity and configured for enhancing Raman spectroscopy via surface plasmon resonance, the optical fibers including distal ends adjoining the cavity and in opposing relation to the probe surface;
    positioning the probe assembly within body tissue;
    causing monochromatic light having a first wavelength to be emitted by one or more of the optical fibers through the cavity and towards the nanostructures;
    generating surface enhanced Raman scattered light within the cavity; and
    conveying, via one or more of the optical fibers, the surface enhances Raman scattered light generated within the cavity to a detector for spectral analysis of the scattered light.

2. The method of claim 1, wherein the distal end of one or more of the optical fibers includes a gradient index lens, further including focusing the emitted monochromatic light using the gradient index lens on the nanostructures configured for enhancing Raman spectroscopy.

3. The method of claim 2, further including positioning a catheter having a distal end in proximity to the probe assembly and introducing a pharmaceutical preparation into the body tissue through the distal end of the catheter.

4. The method of claim 1, further including causing light stimulation of the body tissue by causing the one or more of the optical fibers to emit monochromatic light at a target displaced from the nanostructures configured for enhancing Raman spectroscopy and through a transparent region of the probe housing and into the body tissue, the transparent region of the probe housing including an anti-reflection coating.

5. The method of claim 1, wherein the probe assembly further includes one or more electrodes mounted to the probe housing, further including subjecting the body tissue to electrical stimulation using the electrodes.

6. The method of claim 5, wherein the electrodes comprise metal rings positioned distal to the cavity and attached to an outer surface of the probe housing.

7. The method of claim 5, wherein the electrodes comprise metal rings positioned proximal to the cavity and attached to an outer surface of the probe housing.

8. The method of claim 2, further including causing light stimulation of the body tissue by causing the one or more of the optical fibers to emit monochromatic light having a second wavelength different from the first wavelength into the body tissue.

9. The method of claim 2, wherein the nanostructures are comprised of nanorods extending within the cavity.

10. The method of claim 9, wherein the nanorods have a pitch ratio of at least four, further including admitting inter-cellular fluids or the body tissue within the cavity and between the nanostructures and the distal ends of the optical fibers.

11. The method of claim 9, further including anchoring the probe assembly within the body tissue using the nanorods.

12. The method of claim 1, wherein positioning the probe assembly within body tissue is conducted in vivo.

13. The method of claim 1, wherein the monochromatic light is in the terahertz spectrum, further including causing macromolecules to enter the cavity.

14. The method of claim 1, wherein the probe housing includes a distal housing portion, the distal housing portion including a proximally facing surface bounding a distal end of the cavity and having a first area, the probe surface comprising the nanostructures being adjacent to the proximally facing surface and having a second area, the first area greatly exceeding the second area, further including emitting light from one of the optical fibers towards and focused on a target within the proximally facing surface and displaced from the probe surface comprising the nanostructures.

\* \* \* \* \*